United States Patent [19]

Shinohara et al.

[11] 4,231,963
[45] Nov. 4, 1980

[54] PROCESS FOR PRODUCING AMINOPHENOL ETHER

[75] Inventors: Akira Shinohara, Shimizu; Nobuhide Wada; Yukio Tokunaga, both of Shizuoka; Chihiro Yazawa, Yokohama, all of Japan

[73] Assignee: Ihara Chemical Industry Company, Limited, Tokyo, Japan

[21] Appl. No.: 81,460

[22] Filed: Oct. 3, 1979

[30] Foreign Application Priority Data

Nov. 2, 1978 [JP] Japan .................. 53-134482

[51] Int. Cl.³ .............................. C07C 85/24
[52] U.S. Cl. ................................ 564/443
[58] Field of Search ................. 260/575, 571

[56] References Cited

U.S. PATENT DOCUMENTS

| | | | |
|---|---|---|---|
| 3,567,781 | 3/1971 | Clark | 260/575 X |
| 3,992,432 | 11/1976 | Napier et al. | 260/465.1 |
| 4,105,797 | 8/1978 | Schneider et al. | 260/571 X |
| 4,124,640 | 11/1978 | Shinohara et al. | 260/575 |

FOREIGN PATENT DOCUMENTS

| | | | |
|---|---|---|---|
| 1062261 | 3/1967 | United Kingdom | 260/571 |
| 1154816 | 6/1969 | United Kingdom | 260/575 |

OTHER PUBLICATIONS

Nodzu et al., "Nihon Yakugaku Zasshi," vol. 74, pp. 872-875, (1954).
Kadara et al., "J. Org. Chem.," vol. 22, pp. 333-334 (1957).

*Primary Examiner*—John Doll
*Attorney, Agent, or Firm*—Oblon, Fisher, Spivak, McClelland & Maier

[57] ABSTRACT

An aminophenol ether having the formula

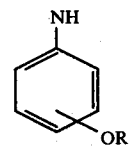

is produced by reacting an alkali aminophenolate having the formula

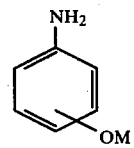

wherein M represents an alkali metal atom; with an organic halide having the formula

R-X wherein R represents a lower alkyl group, a lower alkenyl group or benzyl group; and X represents a halogen atom in substantially anhydrous condition in the presence of an alkali metal hydroxide and a quaternary salt selected from the group consisting of quaternary ammonium salts and quaternary phosphonium salts.

2 Claims, No Drawings

PROCESS FOR PRODUCING AMINOPHENOL ETHER

BACKGROUND OF THE INVENTION

1. Field of the Invention

The present invention relates to a process for producing an aminophenol ether in high selectivity and high yield.

2. Description of the Prior Arts

Aminophenol ethers are useful as starting materials and intermediates for medicines, agricultural chemicals and perfumes. Various processes have been known. For example, it has been known to produce an aminophenyl alkyl ether by directly reacting an aminophenol with alkyl halide. However, in accordance with this process, it is difficult to selectively produce only aminophenyl alkyl ether in high yield since by-products of (b) N-alkylaminophenol and (c) N-alkylaminophenyl alkyl ether are producted together with the object compound of aminophenyl alkyl ether as shown in the following reaction formula

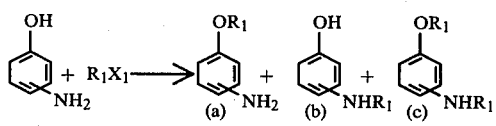

wherein $R_1$ represents an alkyl group; and X represents a halogen atom.

In order to dissolve these difficulties, the following processes have been proposed. (1) An aminophenyl alkyl ether is produced by protecting an amino group of aminophenol to convert it an acetamide group by an acetylation and then hydrolyzing the acetamido group. (See Nippon Yakugaku Zasshi 74 (1954) pages 872 to 875).

(2) An aminophenyl alkyl ether is produced by converting a hydroxyl group of aminophenol to sulfonic ester group ($-SO_3Ar$) by reacting sulfochloride and reacting a metal alcoholate as an alkylating agent. (See Nippon Yakugaku Zasshi 74 (1954) pages 872 to 875).

(3) An aminophenyl alkyl ether is produced by directly alkylating aminophenol by using a dialkyl sulfate as an alkylating agent. (See J. of Organic Chemistry Vol. 22 (1957) pages 333 to 334).

However, the process (1) has the disadvantage of requiring many steps so as to cause a high cost for producing the object compound of aminophenyl alkyl ether. Thus, the process is not satisfactory as an industrial process. The processes (2) and (3) have respectively the disadvantage that the production of the by-products of N-alkylaminophenol and N-alkylaminophenyl alkyl ether can not be satisfactorily prevented to be low selectivity and low yield of aminophenyl alkyl ether.

SUMMARY OF THE INVENTION

It is an object of the present invention to overcome the disadvantages of the conventional processes. It is another object of the present invention to produce an aminophenol ether in high selectivity and high yield in economical process.

The foregoing and other objects of the present invention have been attained by providing a process for producing an aminophenol ether which comprises reacting an alkali aminophenolate having the formula

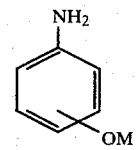

wherein M represents an alkali metal atom; with an organic halide having the formula

R-X wherein R represents a $C_1-C_6$ alkyl group, a $C_1-C_6$ alkenyl group or benzyl group; and X represents a halogen atom in substantially anhydrous condition in the presence of an alkali metal hydroxide and a quaternary salt selected from the group consisting of quaternary ammonium salts and quaternary phosphonium salts.

DETAILED DESCRIPTION OF THE PREFERRED EMBODIMENTS

In the process of the present invention, the following compounds are used.

Suitable alkali aminophenolates include sodium aminophenolates, potassium aminophenolates and lithium aminophenolates.

Suitable organic halides having the formula RX include alkyl halides having a straight chain or branched $C_1-C_6$ alkyl group such as methyl, ethyl, propyl, isopropyl, butyl, isobutyl, sec-butyl, pentyl, isopentyl, hexyl and heptyl groups; and alkenyl halides having a $C_1-C_6$ alkenyl group such as allyl, isopropenyl, 1-butenyl, 2-butenyl and 2-pentenyl group; and benzyl halide. The halogen atom is preferably chlorine or bromine atom.

When isopropyl halide is used, it is possible to use it as a solvent by using excess of the halide.

Suitable alkali metal hydroxides used in the process of the present invention include sodium hydroxide, potassium hydroxide and lithium hydroxide which can be used for the reaction in the form of solid such as pellets, powder and flake.

Suitable quaternary ammonium salts and quaternary phosphonium salts used in the process of the present invention include benzyltrialkylammonium salts, benzyltrialkylphosphonium salts, tetraalkylammonium salts, tetraalkylphosphonium salts, triphneylalkylphosphonium salts and triphenylbenzylphosphonium salts such as benzyltriethylammonium bromide, benzyltributylammonium chloride, benzyltriamylammonium chloride, benzyltrioctylammonium chloride, trioctylmethylammonium chloride, isobutyltributylammonium bromide, hexadecyltributylphosphonium bromide, tetrapropylammonium bromide, tetrabutylammonium chloride, tetraamylammonium bromide, tetraamylammonium chloride, tetrahexylammonium bromide and tetrabutylphosphonium chloride. It is preferable to select the quaternary ammonium salt or the quaternary phosphonium salt from benzyl tri-$C_1-C_{16}$ alkylammonium salts, tetra-$C_1-C_{16}$ alkylammonium salts, triphenylbenzylphosphonium salts, benzyl tri-$C_1-C_{16}$ alkylphosphonium salts, tetra-$C_1-C_{16}$ alkylphosphonium salts, and triphenyl $C_1-C_{16}$ alkylphosphonium salts.

In order to perform smoothly the reaction in the process of the present invention, it is preferable to use an organic solvent.

Suitable solvents include organic solvents except ketones and alcohols; for example, pyridine, tetrahydrofuran dioxane, acetonitrile, benzene, toluene, xylene, chlorobenzene, dichlorobenzene, chlorotoluene, chloroform and carbon tetrachloride.

The reaction of the present invention can be carried out by stirring an alkali aminophenolate and an organic halide in the presence of a solid alkali metal hydroxide and a quaternary ammonium salt or a quaternary phosphonium salt in an organic solvent.

The reaction can be carried out under the atmospheric pressure. The reaction temperature is depending upon a kind of a solvent and is usually lower than 80° C. The reaction time can be selected from a range of 1 to 20 hours as desired.

A ratio of the organic halide to the alkali aminophenolate can be stoichometrically equi-mole and preferably 1.1 to 8.0 mole of the organic halide to 1 mole of the alkali aminophenolate as excess of the organic halide.

It is preferable to use 0.5 to 5.0 mole of the alkali metal hydroxide to 1 mole of the alkali aminophenolate.

It is preferable to use more than 1 mole % preferably about 5 mole % of the quaternary ammonium salt or the quaternary phosphonium salt to 1 mole of the alkali aminophenolate.

It is preferable to use 250 to 2,000 ml. of the solvent to 1 mole of the alkali aminophenolate.

In the process of the present invention, the solid alkali metal hydroxide remained after the reaction is removed by a filtration or a liquid separation followed by a dissolution with water, etc. Then, the solvent is removed to obtain a crude aminophenol ether. The crude aminophenol ether can be purified by a distillation.

The process of the present invention can be also attained by reacting aminophenol with the alkali metal hydroxide in the presence of a quaternary salt selected from the group consisting of the quaternary ammonium salts and the quaternary phosphonium salts in a solvent to obtain the alkali aminophenolate and removing the resulting water and adding the organic halide with or without adjusting an alkali metal hydroxide.

In the process of the present invention, water is not used as the solvent and the reaction is carried out in substantially anhydrous condition to obtain the object compound of the aminophenol ether in high selectivity and high yield.

In the process of the present invention for producing the aminophenol ether by reacting the alkali aminophenolate with the organic halide, the reaction is carried out in substantially anhydrous condition in the presence of the alkali metal hydroxide and the quaternary ammonium salt or the quaternary phosphonium salt. The production of the by-product is substantially controlled to obtain the object compound of the aminophenol ether in high selectivity and high yield to be excellent effect.

The present invention will be further illustrated by certain examples and references which are provided for purposes of illustration only and are not intended to be limiting the present invention.

EXAMPLE 1

In a round bottom flask equipped with a stirrer and a thermometer, 13.1 g (0.1 mole) of sodium 3-aminophenolate, 2 g. (0.05 mole) of sodium hydroxide pellet, 50 g. (0.64 mole) of isopropyl chloride, 1.68 g. (0.005 mole) of tetrapentylammonium chloride and 100 ml. of chlorobenzene as the solvent were charged. The mixture was stirred at 60° C. to react them. After the reaction for 10 hours, 70 ml. of water was added to the reaction mixture. After a phase separation and a washing with water, the solvent and isopropyl chloride were distilled off to obtain 15.0 g. of crude 3-aminophenyl isopropyl ether. According to a gas chromatography analysis, the product had a purity of 99.5% and 0.5% of the by-product of N-isopropyl 3-aminophenyl isopropyl ether was found. The crude yield was 100% to be remarkably high yield and high selectivity.

The crude product was separated and purified by a distillation to obtain 14.9 g. of 3-aminophenyl isopropyl ether having a boiling point of 119° C./10 mmHg. The yield was 98%.

EXAMPLE 2

In accordance with the process of Example 1 except using each quaternary ammonium salt or each quaternary phosphonium salt shown in Table 1 instead of tetrapentylammonium chloride, 3-aminophenyl isopropyl ether was produced. The result are shown in Table 1.

TABLE 1

| Exp. | Quaternary salt | Purity (%) | Yield (%) |
|---|---|---|---|
| 2 | benzyltributylammonium chloride | 99.5 | 97.0 |
| 3 | benzyltripentylammonium chloride | 99.0 | 97.5 |
| 4 | benzyltrioctylammonium chloride | 99.0 | 96.5 |
| 5 | isobutyltributylammonium chloride | 99.5 | 94.0 |
| 6 | hexadecyltributylphosphonium bromide | 98.5 | 98.5 |
| 7 | tetrapropylammonium bromide | 99.0 | 93.7 |
| 8 | tetrapentylammonium bromide | 99.0 | 97.8 |
| 9 | tetrahexylammonium bromide | 98.5 | 98.0 |
| 10 | tetrabutylphosphonium chloride | 98.5 | 99.0 |

EXAMPLES 11 to 25

In accordance with the process of Example 1 except using each alkali aminophenolate and each organic halide shown in Table 2, each aminophenol ether was produced.

The results are shown together with the alkali aminophenolates and the organic halide in Table 2.

TABLE 2

| Exp. | Alakli aminophenolate | Organic halide | Aminophenol ether | Purity (%) | Yield (%) |
|---|---|---|---|---|---|
| 11 | sodium 2-aminophenolate | methyl chloride | 2-aminoanisole | 98.0 | 90.0 |
| 12 | sodium 3-aminophenolate | " | 3-aminoanisole | 99.5 | 97.0 |
| 13 | sodium 4-aminophenolate | " | 4-aminoanisole | 99.0 | 98.5 |
| 14 | potassium 3-aminophenolate | " | 3-aminoanisole | 98.5 | 97.0 |
| 15 | potassium 4-aminophenolate | " | 4-aminoanisole | 98.5 | 96.5 |
| 16 | lithium 3-aminophenolate | " | 3-aminoanisole | 98.0 | 95.0 |

TABLE 2-continued

| Exp. | Alakli amino-phenolate | Organic halide | Aminophenol ether | Purity (%) | Yield (%) |
|---|---|---|---|---|---|
| 17 | sodium 3-aminophenolate | propyl bromide | 3-propoxy-aniline | 98.0 | 98.5 |
| 18 | " | isobutyl chloride | 3-isobutyoxy-aniline | 98.5 | 98.5 |
| 19 | " | pentyl chloride | 3-aminophenyl pentyl ether | 98.5 | 98.5 |
| 20 | " | hexyl chloride | 3-aminophenyl hexyl ether | 98.5 | 98.5 |
| 21 | " | allyl bromide | 3-aminophenyl allyl ether | 99.0 | 98.0 |
| 22 | " | 2-pentenyl chloride | 3-aminophenyl 2-pentenyl ether | 95.0 | 96.5 |
| 23 | " | benzyl chloride | 3-aminophenyl benzyl ether | 94.5 | 97.0 |
| 24 | potassium 3-aminophenolate | propyl chloride | 3-aminophenyl propyl ether | 98.5 | 96.5 |
| 25 | " | benzyl chloride | 3-aminophenyl benzyl ether | 96.0 | 97.5 |

REFERENCE 1

A mixture of 21.8 g. of 3-aminophenol, 39.3 g. of isopropyl chloride, 16 g. of sodium hydroxide and 150 ml. of methanol was stirred at 85° C. for 5 hours to react them. After the reaction, the solvent and isopropyl chloride were distilled off to obtain 11.2 g. of crude 3-aminophenyl isopropyl ether.

According to a gas chromatography analysis, the purity of 3-aminophenyl isopropyl ether was 75.6% and the product contained 11.5% of N-isopropyl-3-aminophenol and 12.8% of N-isopropyl-3-aminophenyl isopropyl ether. The yield was 36.2%.

REFERENCE 2

In accordance with the process of Example 1 except using 48.0% aqueous solution of sodium hydroxide, the reaction was carried out to obtain a crude 3-aminophenyl isopropyl ether having a purity of 80.0% (containing 20.0% of N-isopropyl 3-aminophenyl isopropyl ether). The yield was 45%.

REFERENCE 3

In accordance with the process of Example 1 except that tetrapentylammonium chloride was not incorporated, the reaction was not substantially performed.

REFERENCE 4

In accordance with the process of Example 1 except that methanol was used instead of chlorobenzene, the reaction was not substantially performed.

We claim:

1. A process for producing an aminophenol ether which comprises reacting an alkali aminophenolate having the formula

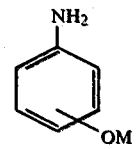

wherein M represents an alkali metal atom; with an organic halide having the formula

R-X wherein R represents a lower alkyl group, a lower alkenyl group or benzyl group; and X represents a halogen atom in substantially anhydrous condition in the presence of an alkali metal hydroxide and a quaternary salt selected from the group consisting of quaternary ammonium salts and quaternary phosphonium salts.

2. A process for producing an aminophenol ether according to claim 1 wherein the quaternary ammonium salt or the phosphonium salt is selected from the group consisting of benzyltrialkylammonium salts, tetraalkylammonium salts, benzyltrialkylphosphonium salts tetraalkylphosphonium salts, triphenylalkylphosphonium salts, and triphenylbenzylphosphonium salts.

* * * * *